United States Patent [19]

Schrems et al.

[11] Patent Number: 4,610,629

[45] Date of Patent: Sep. 9, 1986

[54] APPARATUS FOR DETERMINING THE DESIRED POSITION OF TEETH

[76] Inventors: Hans T. Schrems; Gabriele Schrems-Adam, both of Dechbettener Strasse 1, D-8400 Regensburg 1, Fed. Rep. of Germany

[21] Appl. No.: 639,968

[22] Filed: Aug. 10, 1984

[30] Foreign Application Priority Data

Aug. 11, 1983 [DE] Fed. Rep. of Germany ....... 3329084

[51] Int. Cl.⁴ ............................................. A61C 19/04
[52] U.S. Cl. ........................................ 433/72; 433/56; 433/213
[58] Field of Search ................... 433/72, 56, 197, 196, 433/213, 71; 33/174 D

[56] References Cited

U.S. PATENT DOCUMENTS

| | | | |
|---|---|---|---|
| 1,246,408 | 11/1917 | Fish | 433/72 |
| 1,840,703 | 1/1932 | Cunningham | 433/71 |
| 2,138,254 | 11/1938 | Mink | 433/56 |
| 2,219,559 | 10/1940 | Lentz | 433/56 |
| 2,290,482 | 7/1942 | Neil | 433/72 |
| 2,334,643 | 11/1943 | Moore | 433/56 |
| 2,491,136 | 12/1949 | Salzmann | 433/72 |
| 2,548,817 | 4/1951 | Raiche | 433/72 |
| 2,787,837 | 4/1957 | Gelfand | 433/72 |
| 3,407,501 | 10/1968 | Alexander | 433/72 |
| 3,439,421 | 4/1969 | Perkowski | 433/56 |
| 3,579,832 | 5/1971 | Cooper | 433/72 |
| 3,879,849 | 4/1975 | Schwartz et al. | 433/72 |
| 4,352,663 | 10/1982 | Lee | 433/56 |

FOREIGN PATENT DOCUMENTS 558881 9/1930 Fed. Rep. of Germany ... 33/174 D

OTHER PUBLICATIONS

"Design of Arch Form and Details for Bracket Placement" by Robert M. Ricketts, D.D.S., M.S.–Copyright 1979.

Primary Examiner—John J. Wilson
Attorney, Agent, or Firm—Flynn, Thiel, Boutell & Tanis

[57] ABSTRACT

In the dental area or other dental problem situations (laboratory, orthodontics, jaw orthopedics, prosthetics, restorative dentistry, surgery) to make the desired position of the teeth recognizable at centric occlusion in centric relation (centric relation occlusion), a set of templates (A, B, C, D, etc.) is provided, whereby each template includes markings (1u, 2ru, to 6ru, 2lu to 6lu, 10, 2ro to 6ro, 2lo to 6lo), which correspond with the proximal contact points of the teeth in the desired position. To this end, each of the templates (A, B, C, D, etc.) is dimensioned according to a different tooth arch length and a different tooth arch form, whereby all templates (A, B, C, D, etc.) of the set cover substantially all jaw and tooth arch forms and jaw and tooth arch sizes which occur in patients.

10 Claims, 4 Drawing Figures

MANDIBULAR CAST (UNDER JAW)

MAXILLARY CAST (OVER JAW)

APPARATUS FOR DETERMINING THE DESIRED POSITION OF TEETH

FIELD OF THE INVENTION

The invention relates to an apparatus for determining the desired position of the teeth in tooth position adjusting (e.g., tooth straightening).

BACKGROUND OF THE INVENTION

Such an apparatus is known from U.S. Pat. No. 3,879,849. The known apparatus consists of several bowor divider-like gauge members. If for example six gauge members are provided, then one proceeds in such a manner as to adjust the first gauge member to the transverse desired distance between for example the first premolars (bicuspids), the second gauge member to the transverse desired distance between the second molars and the third gauge member to the sagittal desired distance between the first premolar and the second molar of one side of the lower jaw (mandible). The three further gauge members are adjusted in a suitable manner for the upper jaw (maxilla).

However, with this known apparatus it is hardly possible (or at best only in an incomplete manner) in view of the tooth positions to monitor the success of an orthodontic treatment. Since the possible position change of teeth and their roots mainly depends on the spacial position of the teeth in the bone (alveolar process), an auxiliary means for the planning of orthodontic tooth movements, which does not refer to the skeletal (bone) conditions, cannot be used effectively clinically and therapeutically. In the known apparatus there does not exist any spacial relationship with respect to the skeletal base. Rather, since only the desired distance between specific reference teeth is detected by the known apparatus, in the orthodontic treatment lateral, sagittal and vertical shiftings of the reference teeth with respect to the skeletal base may possibly occur without being detected with the known apparatus. Furthermore, movements of those groups of teeth, which do not serve as reference teeth are not detected at all.

The basic purpose of the present invention is to provide an apparatus, with which the desired position of all teeth during the tooth position adjusting (orthodontic therapy) can be determined exactly, namely that it can be indicated in consideration of a possibly still occurring growth to what degree and in which direction must which teeth be moved, so that the ideal maximum intercuspation occlusion is achieved, namely a maximum intercuspation in the terminal hinge axis position or centric occlusion in centric relation (centric relation occlusion).

Thus, the inventive apparatus includes a set of templates covering substantially the entire jaw and tooth size range occurring in patients.

The templates, of which the inventive apparatus is composed, are relatively simply made. The following knowledge is thereby the basis of the inventive apparatus. The position of the terminal hinge axis position is determined substantially by the tooth arch length, namely the sum of the mesiodistal diameter of all teeth, and by the tooth arch form (shape). The position of the occluding parts of the teeth, thus the cusp tips, the grooves and fissures (fossae) and the incisal edges of the teeth, is thus almost always the same for a predetermined tooth arch length and tooth arch form.

Furthermore, tooth position adjusting is possible only within the tolerances allowed by the skeletal base. The tooth position adjusting sequence therefore must start out from the teeth with the least alveolar tolerances.

BRIEF DESCRIPTION OF THE DRAWING

One embodiment of the inventive apparatus will be discussed in greater detail hereinafter in connection with the drawings in which.

DETAILED DESCRIPTION

Figure 1:
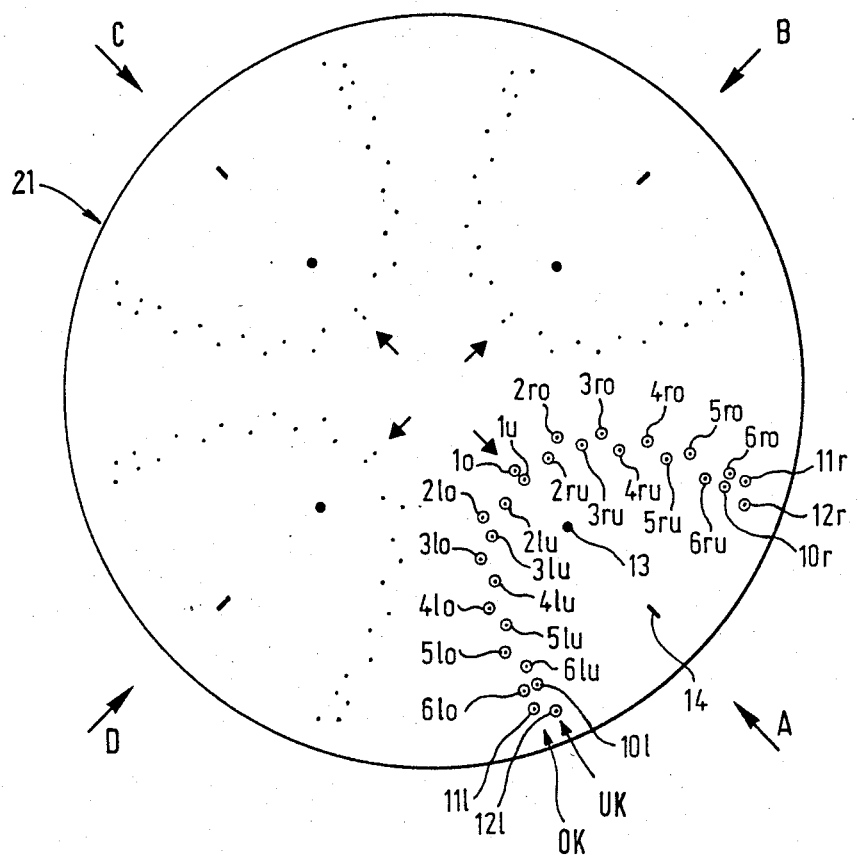
FIG. 1 is a plan view of a disk with four templates A, B, C and D and embodying the invention.

Four such templates, as at A, B, C and D in the drawing, for four different tooth-width types for the three most important basic tooth arch forms according to Ricketts ("Design of Arch Form and Details of Bracket Placement"; 1979, Page 4, published by Rocky Mountains/Orthodontics) practically cover all non-extraction cases.

The templates A, B, C and D differ only from one another by each being designated for a different tooth arch length and tooth arch form. To simplify matters only the template A is therefore discussed in detail.

The marking points $1u$, $2ru$, to $6ru$ and $2lu$ to $6lu$ of the inner arch (mandible) of the template A thereby reproduce the proximal contact points between the two central incisors, between the central and the lateral incisor, between the lateral incisor and the canine, between the canine and the first premolar, between the first premolar and the second premolar and between the second premolar and the first molar of the lower jaw (mandible), namely for the left (l) and for the right (r) side. The marking points $1o$, $2ro$ to $6ro$ and $2lo$ to $6lo$ of the outer arch (maxilla) reproduce the proximal contact points between the corresponding teeth of the upper jaw (maxilla). The reproduction of the marking points $1$, $2ru$ to $6ru$ and $2lu$ to $6lu$ of the inner arch (mandible) and the reproduction of the marking points $1o$, $2ro$ to $6ro$ and $2lo$ to $6lo$ of the outer arch (maxilla) thereby represents a projection of said proximal contact points in the horizontal plane.

The marking points $10r$ and $11r$ and $10l$ and $11l$, however, correspond with the two mesiobuccal cusp tips of the first molars of the mandible and the maxilla. Thus, the proximal contact points between the first and the second molars are not marked on this template. Of course, markings for other proximal contact points of the teeth may also be missing. However, preferred is the illustrated embodiment, in which, aside from the proximal contact points between the first and second molars, and between the second and third (if present) molars, markings for all proximal contact points of the teeth of the upper and lower jaw are provided.

The endmost point $12r$ or $12l$ represents the central point of the first upper molar. The central point is a reference point which is used in orthodontics and in anthropology. It corresponds with the lowermost point of the central fissure and lies in the point of intersection between the central fissure and the transverse fissure which extends between the two buccal cusps.

Furthermore, the template has two markings 13 and 14, which characterize the raphemedian plane.

The marking points 1u, 2ru to 6ru, 2lu to 6lu, 1o, 2ro to 6ro, and 2lo to 6lo thereby reproduce the proximal contact points at an ideal set of teeth for that respective tooth arch length and tooth arch form. The same is valid for the marking points 10r, 11r, 10l and 11l for the cusp tips of the first molars and for the last points 12r and 12l on the template A.

The disk, on which the templates A, B, C and D are arranged, preferably comprises a transparent and flexible plastic 21.

OPERATION

In applying the inventive apparatus one can proceed for example as follows:

With the help of a centric occlusion wax bit (interocclusal record which has been bitten through) occurs in the orthodontics the relation of the maxillary cast and the mandibular cast in the maximum intercuspation (centric occlusion, habitual occlusion). However, since the relation of the upper cast and the lower cast in the centric occlusion cannot be reproduced reliably and since in almost all cases dependency on existing tooth misalignments (malocclusion) through the influence of the neuromuscular system leads to spacial misalignment (eccentric position) of the manidble, basically a centric interocclusal record is needed, which permits a reproducible relation of the maxilla and the mandible without the danger of the excursive movement of the mandible. With this, the relation of the maxillary cast and the mandibular cast in the terminal hinge axis position becomes possible and also to judge the position of maxillary teeth and mandibular teeth in the terminal hinge axis position.

The tooth arch length of the patient is determined. One can proceed to do so for example by the so-called SI-method, namely the sum of the mesiodistal diameters of the upper four incisors is determined, from which empirically results the tooth arch length.

Furthermore the tooth arch form of the patient is determined. The tooth arch form can be determined for example with the help of the shape of the face or with the form of the existing bone base (alveolar process). The division into four or five different basic tooth arch forms per tooth arch length is thereby sufficient. For example with five basic tooth arch forms practically 100% of the cases are covered (Ricketts in "Design of Arch Form and Details of Bracket Placement"; 1979, Page 4, published by Rocky Mountains/Orthodontics).

Using the measured tooth arch length and the determined tooth arch form, the respective template A, B, C, D . . . is now selected. In the case of deviations and discrepancies between the central incisors and lateral incisors or the maxillary and mandibular teeth (for example Bolton discrepancy) another template type which considers these circumstances is used.

As mentioned above, in the orthodontic treatment one must start out from the teeth with the least alveolar tolerances. The most limited is the position change in the alveolar process thereby in the mandibular incisors due to the symphysis configuration. The proximal contact point between the central incisors of the mandible represents thereby advantageously the starting point of the orthodontic treatment using the inventive apparatus.

The movement tolerance of the central incisors of the mandible in the alveolar process can be determined exactly with a lateral X-ray picture (cephalometric head film) and a orthodontic cast (model) analysis considering the individual situation.

Using the so determined therapeutic limited possibility of movement now the desired proximal contact point between the central incisors of the mandible is determined and the mandibular cast is provided with a corresponding marking point. Of course, possibly existing alveolar centerline misalignments must be considered in the determining of the therapeutic desired proximal contact point between the lower incisors, as also must be considered the possibility of growth whereby the growth direction is determined by using the familiar growth prediction methods which are common in the orthodontics and jaw orthopedics based on cephalometric and other data.

Figure 2:
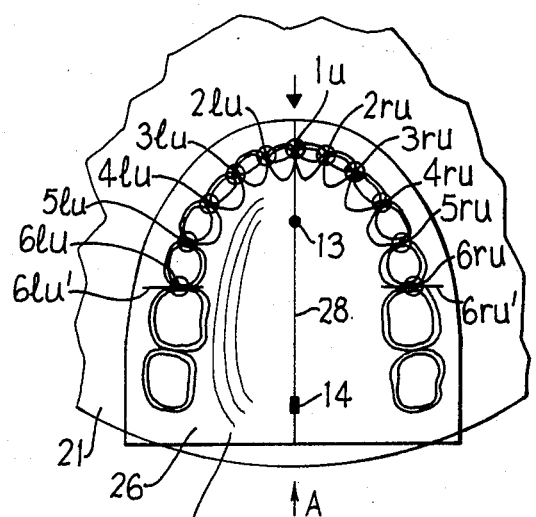
FIG. 2 is a plan view of a mandibular casting.

As seen in FIG. 2, the marking point on the mandibular cast 26 for the desired proximal contact point between the central incisors and the marking point 1u on the respective template (e.g., A) of the inventive apparatus are now brought to coincidence (are aligned), namely by aligning corresponding markings 13 and 14 of the template with the straight line 28 along which the raphemedian plane intersects the mandibular cast 26.

The straight line at which the raphemedian plane intersects the lower cast can be determined for example by providing bores in the palate suture on the upper cast at two points which are remote from one another, into which bores marking pins are inserted. The upper cast and lower cast are then arranged in a terminal hinge axis position preferably in an articulator, whereby the two marking pins in the upper cast produce two corresponding markings on the lower cast, which then represents the raphemedian plane on the lower cast.

If the marking point 1u of the template (denoting the proximal contact point between the two central incisors of the mandible) coincides with the marked desired proximal contact point for the two central incisors on the mandibular cast and if the markings 13 and 14 of the template coincide with the raphemedian plane of the mandibular cast, the desired position of the proximal contact points between the remaining teeth of the mandible in ideal tooth set arrangement is then determined by the marking points 2ru to 6ru and 2lu to 6lu, as is also the desired position of the cusp tips 10r, 11r and 10l and 11l of the first molars of the mandible.

This means that it is possible with the inventive apparatus to determine exactly which teeth must be moved in which direction and to what degree, referred to the projection in the horizontal plane, during the tooth position adjusting.

Figure 3:
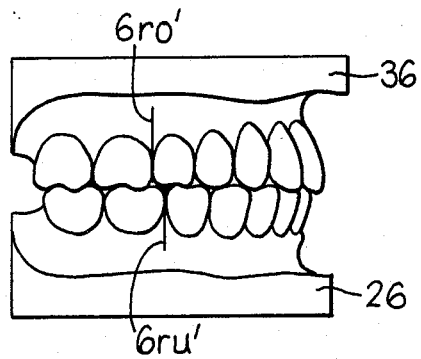
FIG. 3 is a side view of superposed mandibular and maxillary castings.

In order to assure a long-term strong and functional occlusion and chewing function, the occlusion in centric relation in a tooth to two tooth relationship in (Angle-class-I-occlusion) is desirable. From a predetermined ideal occlusion of the mandible in the individual situation, there results the correct maxillary ideal occlusion and the correct spacial position relationship of the maxillary teeth clearly in the centric relation of the mandible to the maxilla. The determining of the desired position of the maxillary teeth in the central relation can be found as follows:

The desired proximal contact points of the mandibular teeth in their projection in the horizontal plane, can be marked by projection in the median plane on the lower cast. In particular, the proximal contact point between the lower second premolars and the first molars can be determined on both the left and right sides. On an upper cast 36 which is mounted in a terminal hinge axis position (centric relation) in the articulator, or alternately on an upper cast associated through a centric interocclusial wax record with the mandible, it is possible through the sagittal proximal contact point of the lower first molar, which sagittal proximal point is indicated on the lower cast, to draw the sagittal desired position (as at 6ro' in FIG. 3) of the proximal contact point 6ro, 6lo between the upper second premolar and the first molar in the so-called neutral occlusion (Angle-class-I-occlusion), or neutral tooth position, through projection in the median plane on the cast, on both the right and left sides.

The desired position of the proximal contact point between the first molars and the adjacent premolars can be drawn for extraction cases (for example Angle-class-II-occlusion for extraction of two upper premolars). In general, the inventive apparatus is, of course, also applicable after carrying out an extraction therapy.

In centric relation of a mandibular tooth which is in, or is drawn into, ideal occlusion, the optimum position of the respective maxillary antagonists (maxillary teeth opposing such mandibular tooth) is defined therewith.

Figure 4:
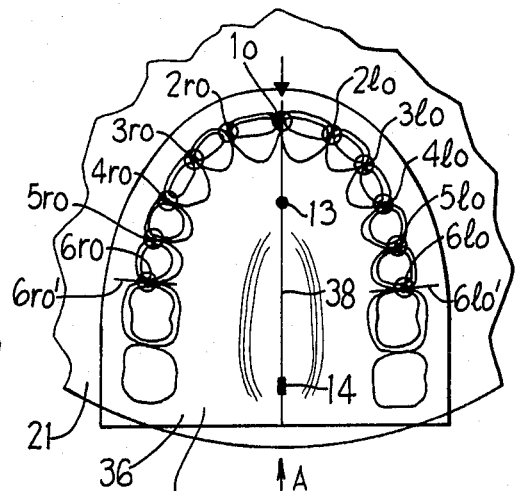
FIG. 4 is a plan view of a maxillary casting.

The respective markings of the upper tooth arch row of the template for the proximal contact points of said teeth of the maxilla (as represented on the maxillary cast 36 as seen in FIG. 4) and the markings 13 and 14 for the raphemedian plane are then respectively brought into coincidence with the proximal contact points of said teeth, which are in ideal occlusion, and with the palate suture 38 of the maxilla. In this manner one obtains the ideal arrangement of the maxillary teeth preferably by superposing the template points 6ro and 6lo in the new therapeutic sagittal desired position.

A a result, the desired proximal contact points of all remaining teeth of the maxilla are determined by the (further) marking points 1o, 2ro to 5ro, 2lo to 5lo of the template. Thus it can now be determined which teeth of the maxilla must be moved in which direction and to what degree during orthodontic treatment, so that an ideal centric occlusion (centric relation occlusion) is created.

In the case of the term "proximal contact point", we do not deal in every instance with an actual contact point, but rather, because of anatomic variance, with a point which lies very close to the bucally lying contact point of two teeth. In any case, the proximal contact point lies on the interdental (interproximal) line between two adjacent teeth in the direct vicinity of the buccal contact point of said teeth. The imaginary interdental (interproximal) lines intersect the individual arch form in a correct arrangement of the teeth in each instance at an angle of approximately 90°.

The templates of the inventive apparatus can also be formed by suitable markings on a disk or a film, with which the markings can then be projected on the mandibular cast or the maxillary cast. The templates can for example be provided with suitable holes or all together can be designed skeleton-like in order to mark the therapeutic desired points and/or to assure a spacially correct fixation of the template with respect to the model.

Furthermore, it is possible to form the markings of a template not only by means of projecting desired proximal contact points onto the horizontal plane, but rather a projection onto the median or sagittal plane is also possible. In a projection onto the sagittal plane the desired proximal contact points are also arranged in the form of an arch. Furthermore, other anatomically-morphologically relevant reference points or lines or auxiliary lines are possible as markings for use of treatment means, since for example for the laboratory area other auxiliary means can appear to be advantageous.

The inventive apparatus is suited for determining the desired position of teeth in a known arch form and tooth widths and permits the correct placement of orthodontic treatment elements in all treatment devices during the planning and installing or mounting in the dental laboratory area and permits an early recognition of necessary extractions, tooth arch length deficits and tooth arch discrepancies and permits constant checking on the success of the treatment or lab work. Furthermore, a quantitative detecting of tooth movements, which are to be carried out and which have been carried out, is made possible for the first time. The inventive apparatus can therefore also find technical use for administration and insurance.

With the help of the inventive templates one can, for a given patient, select the specific optimum type units from the available stock of prefabricated treatment devices or treatment parts.

LITERATURE

"The glossary of occlusal terms"
International Academy of Gnathology, Sept. 1979 La Mesa, Calif. 92041, 4323 Palm Avenue
Synonyma:
  upper jaw: maxilla
  lower jaw: mandible

We claim:

1. A method for determining the desired position of the teeth and employing a set of templates, each template being provided with markings which correspond to desired positions of the teeth of the mandible and maxilla, the individual templates differing from each other by having their markings located to correspond to different tooth arch lengths and different tooth arch forms, so that all templates of the set cover substantially all jaw and tooth arch forms and jaw and tooth arch sizes likely to occur in patients, the method comprising:
   (a) making a maxillary casting and a mandibular casting from the teeth of the mandible and maxilla of a patient;
   (b) determining the tooth arch length and the tooth arch form of the patient and from that selecting the relevant template of the set of templates;
   (c) marking a line on the mandibular casting along which the raphemedian plane intersects the mandibular casting, and superposing the template onto the mandibular casting in such a way that a first marking on the template coincides with the desired proximal contact point between two central incisors of the mandibular casting and the template is aligned, by means of alignment markings thereon, with said line marked onto the mandibular casting;
   (d) determining the desired position of the proximal contact points of the remaining teeth of the mandible by means of rightward second to sixth markings and leftward second to sixth markings located on the template and corresponding to the mandible;
   (e) marking on the mandibular casting at least one desired proximal contact point on both the left and right sides in projection of the median plane, and arranging in centric relation the mandibular casting and the maxillary casting, and marking on the maxillary casting at least one desired proximal contact point on both the left and the right sides in projection in the median plane;

(f) superposing the template on the maxillary casting and aligning the alignment markings on the template with the palate suture on the maxillary casting, namely the line on the maxillary casting along which the raphemedian plane intersects the maxillary casting, and with said markings for said proximal contact points on the maxillary casting projected onto corresponding maxilla related markings on the left and right sides on the template; and (g) marking onto the maxillary casting the desired position of the proximal contact points of remaining teeth of the maxilla from corresponding markings on the template, wherein the template has a first set of markings forming an arch comprising said first marking and said right second through sixth markings and said left second through sixth markings with said first marking at the center of the arch and said sixth markings adjacent the spaced apart ends of the arch and corresponding to a mandibular tooth arch form, said template carrying a second arch of similar markings for tooth contact points of the maxilla which markings include said corresponding maxilla related markings on the left and right sides of the template, said arches being superposed one on the other in correspondence to desired superposition of teeth of the mandible with respect to teeth of the maxilla, said alignment markings defining a line extending from said first marking through said alignment markings and substantially bisecting the superposed arches, with the alignment markings between the right and left legs of the superposed arches.

2. Apparatus to determine the need for, and monitor progress in, the repositioning of teeth in a patient, comprising:

initial maxillary and mandibular castings of the teeth of the patient;

a set of templates, each template being provided with markings which correspond to desired positions of the teeth, the individual templates differing from each other by having their markings located to correspond to different tooth arch lengths and different tooth arch forms, said markings on the template including an arch-shaped set of mandibular markings and an arch-shaped set of maxillary markings located in centrically superposed relation with respect to said set of mandibular markings in correspondence to the desired location of the upper and lower rows of teeth of the patient, the templates of the set together covering substantially all jaw and tooth arch forms and jaw and tooth arch sizes normally occurring in patients, a selected one of said templates corresponding to the tooth arch length and tooth arch form of the patient;

a line marked onto the mandibular casting along which line the raphemedian plane intersects the mandibular casting and means on the template for superposing the template on the mandibular casting in a repeatable manner, such means comprising a first marking on the template located as the projection of the desired proximal contact point between the two central incisors of the mandibular casting, and a pair of alignment markings substantially aligned with said first marking and substantially centered in the tooth arch form defined by the markings on the template;

further markings of the mandibular set on the template being positioned at the desired location of the proximal contact points of further teeth of the mandible of the patient, said remaining mandibular markings thus comprising a subset of leftward markings and a subset of rightward markings defining the leftward and rightward legs of the tooth arch;

the mandibular casting being marked with at least one desired proximal contact point on the left and right sides thereof as a projection of corresponding remaining mandibular markings on the left and right side of the arch of mandibular markings on the template, such that the template on which the mandibular casting is accurately located provides by projection of ones of its markings a location to mark on the mandibular casting to indicate the desired location of a proximal contact point between an adjacent pair of teeth on the right and left sides of the tooth arch of the mandibular casting, the mandibular casting and maxillary casting being arrangeable in centric relation in a conventional manner and such that the maxillary casting can be marked with a desired proximal contact point on the left and right sides thereof;

the maxillary casting having a line along which the raphemedian plane intersects the maxillary casting and coresponding to the palate suture, for superposition of the template on the maxillary casting with the alignment markings of the template superposed on the palate suture of the maxillary casting and said markings for said proximal contact points on the left and right sides of said maxillary casting projected on corresponding markings on the left and right sides of the maxillary tooth arch of the template, such that with the maxillary casting so positioned on the template, the desired position of the proximal contact points of the remaining teeth of the maxilla can be projected from the corresponding markings on the maxilla tooth arch of the template onto the maxillary casting;

whereby marks corresponding to the desired locations of the proximal contact points can be marked on the initial set of mandibular and maxillary castings from the selected template to indicate the tooth relocations required during treatment, and whereby the same template can be used with later maxillary and mandibular castings made at later stages of the treatment to detect progress in the tooth relocation treatment.

3. Apparatus for determining the desired position of the teeth of a patient, comprising a set of substantially planar templates, each template having markings which correspond to desired positions of the proximal contact points of the teeth in projection on the horizontal plane, the individual templates differing from each other by having their markings located to correspond to different tooth arch lengths and different tooth arch forms, the templates of the set together covering substantially all jaw and tooth arch forms and jaw and tooth arch sizes, which occur in patients, in which said markings on said template each mark the location of a point on said template, said markings being spaced and defining in centrically superposed relation a mandibulary arch and a maxillary arch.

4. Apparatus according to claim 3, wherein each template has additional markings for cusps of the teeth.

5. Apparatus according to claim 3, wherein each template has additional markings for fissures of the teeth.

6. Apparatus according to claim 3, wherein each template has additional markings for the central points.

7. Apparatus according to claim 3, wherein the templates of the set cover substantially all jaw and tooth arch forms and jaw and tooth arch sizes which occur in primary dentition.

8. Apparatus according to claim 3, wherein the templates of the set cover substantially all jaw and tooth arch forms and jaw and tooth arch sizes, which occur in mixed dentition, namely in a mixture of primary and permanent dentition.

9. Apparatus according to claim 3, wherein a said set of templates is provided for the position of the teeth in the desired position in the sagittal plane and a said set of templates for the position of the teeth in the desired position in the transverse plane.

10. Apparatus according to claim 3, including a disk containing several said templates spaced around the periphery thereof, the control apices of the tooth arches of the several templates being adjacent the central portion of the disk, the left and right ends of each said tooth arch being adjacent the edge of said disk.

* * * * *